United States Patent [19]

Sapse

[11] Patent Number: 5,064,858

[45] Date of Patent: Nov. 12, 1991

[54] PROTECTED COMPLEX OF PROCAINE FOR THE TREATMENT OF SYMPTOMS FROM NARCOTICS ADDICTION, TINNITUS AND ALZHEIMER'DISEASE

[75] Inventor: Alfred T. Sapse, Miami Beach, Fla.

[73] Assignee: Spectrum Pharmaceutical Corporation, Aventura, Fla.

[21] Appl. No.: 578,030

[22] Filed: Sep. 5, 1990

Related U.S. Application Data

[62] Division of Ser. No. 233,247, Aug. 17, 1988, Pat. No. 4,956,391.

[51] Int. Cl.[5] .................. A61K 31/21; A61K 9/14; A61K 9/50
[52] U.S. Cl. .................. 514/536; 424/489; 424/499; 424/502
[58] Field of Search .......................... 514/536

[56] References Cited

U.S. PATENT DOCUMENTS 4,956,391 9/1990 Sapse .................. 514/810

Primary Examiner—Frederick E. Waddell
Assistant Examiner—Diane Gardner
Attorney, Agent, or Firm—St. Onge Steward Johnston & Reens

[57] ABSTRACT

The invention presented is a composition for the treatment of individuals addicted to narcotics or individuals having age-related conditions such as tinnitus and Alzheimer's disease, comprising a protected complex of procaine and a complexing agent for procaine in an amount effective to reduce the withdrawal symptoms of individuals addicted to narcotics or the symptoms of tinnitus and Alzheimer's disease.

16 Claims, No Drawings

PROTECTED COMPLEX OF PROCAINE FOR THE TREATMENT OF SYMPTOMS FROM NARCOTICS ADDICTION, TINNITUS AND ALZHEIMER'DISEASE

This is a division of Ser. No. 233,247, filed on Aug. 17, 1988, now U.S. Pat. No. 4,956,391.

TECHNICAL FIELD

The present invention relates to a composition which comprises a protected complex of procaine (4-aminobenzoic acid 2-(diethylamino)ethyl ester) and complexing agent, and its use in the treatment of narcotics addiction and age-related conditions such as tinnitus and Alzheimer's disease.

Narcotics addiction has become a worldwide societal problem of tremendous proportions. Current programs for the reduction of addiction in individuals involve either so-called "cold turkey" (complete cessation of narcotic use without suitable replacement), or the treatment with substitutes such as methadone. These programs are disadvantageous and have many drawbacks and critics, especially due to the fact that "cold turkey" is viewed as an ineffective means of breaking an addiction and methadone itself is an addicting narcotic. Accordingly, a composition which can be used to treat narcotics addictions by reducing the withdrawal symptoms of recovering addicts will be invaluable in aiding in the breaking of narcotics addictions.

Problems associated with aging have long been studied without effective preventative treatments being developed. Conditions such as tinnitus, which is generally perceived as a ringing, buzzing or whistling in the ear caused by a defect in the auditory nerve and is common in elderly individuals, and Alzheimer's disease, which is a senile dementia believed to be brought about by the aging process, are two such problems for which no known treatment has been shown to be effective. A composition which can ease sufferers of these conditions, therefore, is being widely sought since they affect so many elderly individuals and will be of great benefit.

It has now been found that the compositions of the present invention, and their method of use, are effective at reducing the withdrawal symptoms of recovering narcotics addicts and also at reducing the symptoms of both tinnitus and Alzheimer's disease.

DISCLOSURE OF INVENTION

As noted above, the present invention relates to a composition which comprises a protected complex of procaine and a complexing agent. Procaine is a composition of the formula

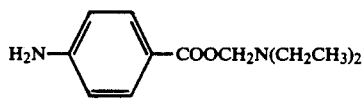

and is commonly prepared by reacting 2-diethylaminoethanol with p-nitrobenzoyl chloride to form 2-diethylaminoethyl p-nitrobenzoate which is then reduced to form 4-aminobenzoic acid 2-(diethylamino)ethyl ester (procaine). Alternatively, procaine can be prepared by esterifying p-aminobenzoic acid with 2-ethylaminoethanol, with sulfuric acid ($H_2SO_4$) used as a catalyst. Several other means of preparing procaine will also be familiar to the skilled artisan.

Generally, procaine is present as a pharmaceutically acceptable acid addition salt thereof for the purposes of increased stability, convenience of crystallization, increased solubility and the like. Preferred pharmaceutically acceptable acid addition salts include those derived from inorganic acids such as hydrochloric, hydrobromic, sulfuric, nitric, phosphoric, perchloric acids and the like as well as organic acids such as tartaric, citric, acetic, succinic, maleic, fumaric acids and the like. Typically, procaine is present as its hydrochloric acid addition salt. When used herein, the term procaine is meant to also include its pharmaceutically acceptable acid addition salts.

It has been found that procaine is effective in treating individuals, especially humans, addicted to narcotics by reducing the withdrawal symptoms experienced during the period of recovery from the addiction. By the term "addicted" or "addiction" is meant the compulsive, uncontrolled use of habit forming drugs. By the term "narcotic" is meant a drug, such as cocaine, heroin, morphine, methadone, marijuana, nalorphine, phenylcyclidine hydrochloride ("PCP" or "angel dust"), naloxone and the like, that dulls the senses, induces sleep and, with prolonged exposure, becomes addictive. Although the mechanism by which procaine reduces withdrawal symptoms in addicts, which commonly include one or more of craving, anxiety, restlessness, insomnia, muscular aching, anorexia, nausea, hot and cold flashes, rhinorrhea, tremors, perspiration, yawning, yen for sleep, gooseflesh, vomiting, diarrhea lacrimation, etc., as would be known to the skilled artisan, is not fully understood, it is believed that procaine has anticortisol activity and, additionally, may compete for and occupy the same acetylcholine receptors as the addictive narcotic. Consequently, procaine is useful in the reduction of addiction in addition to the reduction of symptoms of dependence.

Cortisol is a hormone manufactured by the adrenal gland. It is sometimes referred to as the stress hormone. While variations of cortisol levels are normally experienced and are considered useful in preparing the individual for stress normally encountered, when such stress is continuous or the individual is less resistant to it, the level of cortisol is continuously elevated and deleterious effects occur. Elevated levels of cortisol are found in individuals suffering from depression, alcoholism, drug addiction, and aging in the senile dementia of the Alzheimer's type.

Anti-cortisol drugs are pharmaceutical compounds that can lower the level of cortisol previously elevated, thus bringing about therapeutic effects. Procaine has been found to have such anticortisol effects. Additional compounds through to have anticortisol effects include lidocaine, dilantin (also referred to as phenytoin), vitamin C (ascorbic acid), clonidine HCl (catapress).

Acetylcholine is a neurotransmitter that attaches itself to a certain area of the brain, which is considered to be the center responsible for addiction. Cocaine and other addictive narcotics as well as procaine attach themselves in a competitive way to the acetylcholine receptors. In this competition, the composition which arrives first is first bound. As such, should procaine be introduced first in the body of an individual, it would block the receptor center, thus making it unavailable if and when cocaine or other addictive narcotic is taken. Subsequently, the addictive narcotic is eliminated if taken during the period of treatment with procaine, thus inducing aversion symptoms such as vomiting, muscle cramps, abdominal pain, diarrhea, and other symptoms.

Procaine has also been found to reduce the effects of some age-related conditions such as tinnitus and Alzheimer's disease by reducing the symptoms thereof. The mechanism by which procaine reduces the symptoms of tinnitus and Alzheimer's disease is not fully understood, but it is believed to be related to the anticortisol and anticholinesterase activity of procaine as well as the ability of procaine to inhibit monoamine oxidase (MAO). Cortisol, cholinesterases and MAO have been associated with the effects of aging such as tinnitus and Alzheimer's disease.

The procaine composition of the present invention also comprises a complexing agent capable of forming a protected complex of procaine to prevent unwanted hydrolysis of the procaine which would normally occur if the procaine was not protected. Such hydrolysis results in destruction of the procaine molecule prior to its being able to perform its desired function, i.e., the reduction of symptoms of drug addiction and age-related conditions. Suitable complexing agents are those which form a non-permanent complex with procaine, to permit dissociation of the complex at the site for procaine action (generally believed to be the brain). Such complexing agents include polysaccharides such as dextran, glycols such as polyethylene glycol, ascorbic and pantothenic acid, acetylsalicylic acid, caffeine and amino acids such as isoleucine, alanine, phenylalanine, etc. Most preferred is ascorbic acid and acetylsalicylic acid, although the use of acetylsalicylic acid as the complexing agent in the treatment of tinnitus is to be avoided since acetylsalicylic acid may have some aggravating effects on tinnitus sufferers.

The composition of the present invention generally comprises from about 1% to about 10% by weight of procaine to effectuate the treatments described above. The composition also generally comprises the appropriate amount of complexing agent in order to form the protected complex of procaine described above, typically an amount of about 0.1 to about 3 times the amount of procaine, or about 0.1% by weight to about 30% by weight of the composition, preferably about 0.25% by weight to about 10.0% by weight. For instance, when ascorbic acid is used as the complexing agent, it is generally present at about 100 milligrams to about 200 milligrams per every 400 milligrams of procaine; when acetylsalicylic acid is used as the complexing agent, it is generally present at about 150 milligrams to about 650 milligrams, most preferably about 325 milligrams to about 500 milligrams per 400 milligrams of procaine Advantageously, the composition of the present invention also comprises other components which provide other or synergistic benefits with the procaine complex. Such other components include lidocaine (2-(diethylamino)-N-(2,6-dimethylphenyl)acetamide) which appears to synergistically improve the action of procaine; an anticholinesterase such as pyridostigmine bromide, neostigmine and physostigmine, to provide additional anticholinesterase activity; and an anticortisol agent such as clonidine and dilantin to provide additional anticortisol activity. The presence of these other components is generally in a ratio of procaine to other component of about 0.25:1 to about 50:1, depending on the particular other component, the method of administration (i.e., parenteral, oral, etc.) and the results desired, and would be easily determinable by the skilled practitioner in the art.

Effective amounts of the protected procaine complex of the present invention may be administered by one of a variety of methods, for example, orally as in capsules or tablets, parenterally in the form of sterile solutions or suspensions, and intravenously in the form of sterile solutions. Additionally, other methods of introduction include delivery vehicles such as patches and/or liposomes, suppositories, ion exchange resins, sublingual means, absorbable polymers such as polyethylene glycol compositions, and nasal sprays or drops, and other delivery techniques currently known or under development.

Oral administration can be with an inert diluent or with an edible carrier. The compositions may be enclosed in gelatin capsules or compressed into tablets. For the purpose of oral therapeutic administration, the complex may be incorporated with excipients and used in the form of tablets, troches, capsules, elixirs, suspensions, syrups, wafers, chewing gums and the like. The amount of the inventive composition present is such that a suitable dosage will be obtained. Preferred compositions and preparations according to the present invention are prepared so that an oral dosage unit form contains between about 25 and about 300 milligrams of procaine. The tablets, pills, capsules, troches and the like may also contain the following adjuvants: a binder such as microcrystalline cellulose, gum tragacanth or gelatin; an excipient such as starch or lactose; a disintegrating agent such as alginic acid, corn starch and the like; a lubricant such as magnesium stearate; a glidant such as colloidal silicon dioxide; and a sweetening agent such as sucrose, fructose, saccharin or aspartame may be added or a flavoring agent such as peppermint, methyl salicylate or orange flavoring. When the dosage unit form is a capsule, it may contain, in addition to the above, a liquid carrier such as a fatty oil. Other dosage unit forms may include other various materials which modify the physical form of the dosage unit, for instance, as coating. Thus, tablets or pills may be coated with sugar, shellac, or other enteric coating agents. A syrup may contain, in addition to the protected complex, sucrose or fructose as a sweetening agent and certain preservatives, dyes and colorings and flavorings. Of course, all materials should be pharmaceutically pure and non-toxic in the amounts and ways used.

In making parenteral therapeutic administration, the protected procaine complex may be incorporated into a solution or suspension. These preparations should contain an amount of procaine suitable to ensure that a proper dosage is obtained. Preferred compositions and preparations are prepared such that a parenteral dosage unit contains between about 25 to about 100 milligrams of procaine.

The solutions or suspensions may additionally include the following adjuvants: a sterile diluent such as water for injection, saline solution, fixed oils, polyethylene glycols, glycerine or other synthetic solvents; antibacterial agents such as benzyl alcohol or methyl paraben; antioxidants such as sodium bisulfite; chelating agents such as ethylenediaminetetraacetic acid (EDTA); buffers such as citrates or phosphates; and agents for the adjustment of tonicity such as sodium chloride or dextrose. The parenteral preparation can be enclosed in ampules, disposable syringes or multiple dose vials made of glass or plastic.

Additionally, components of both the oral and parenteral and other forms of administration can include zinc salts, especially zinc citrate, as a buffer (i.e., about 0.5% in both the oral and parenteral preparations); dimethylsulfoxide (DMSO) to enhance epidermal penetration; chlorobutanol as a preservative; and an acid such as hydrochloric acid or a base such as sodium hydroxide to adjust the pH.

Although the primary role of zinc citrate is as a buffer, as indicated above, there may be some positive synergistic effects of the use of zinc citrate with the protected complex of procaine of the present invention for the reduction of both the symptoms of withdrawal from narcotics addiction and the symptoms of age-related conditions such as tinnitus and Alzheimer's disease. In fact, the combination of procaine, ascorbic acid (a preferred complexing agent) and zinc citrate is believed to exert a positive synergistic effect on the treatment of narcotics addiction and age-related conditions, especially age-related conditions, over the effect seen when complexed procaine using a different buffer or complexing agent is used.

The compositions of the present invention are advantageously prepared by combining, in admixture, procaine, the complexing agent for procaine, and any other desired ingredients, as described above, to form the protected complex of procaine.

The following represent examples of parenteral formulations of the compositions of the present invention:

| Procaine HCl | 4 gms |
|---|---|
| Ascorbic Acid | 2 gms |
| Sodium Chloride | 14.652 mg |
| Chlorobutanol | 16.65 mg |
| Water | q.s. to 100 ml |

Hydrochloric Acid and/or Sodium Hydroxide to adjust pH to 3 5;
to prepare a 4% procaine solution.

| Procaine HCl | 2 gms |
|---|---|
| Ascorbic Acid | 1 gm |
| Sodium Chloride | 7.326 mg |
| Chlorobutanol | 8.82 mg |
| Water | q.s. to 100 ml |

Hydrochloric Acid and/or Sodium Hydroxide to adjust pH to 3.5;
to prepare a 2% procaine solution.

| Procaine HCl | 2 gms |
|---|---|
| Acetylsalicylic Acid | 4 gms |
| Sodium Chloride | 7.326 mg |
| Chlorobutanol | 8.82 mg |
| Water | q.s. to 100 ml |

Hydrochloric Acid and/or Sodium Hydroxide to adjust pH to 3.5;
to prepare a 2% procaine solution.

The following example further illustrates and explains the present invention by showing the use of a protected complex of procaine in the treatment of patients addicted to narcotics.

EXAMPLE

Eleven individuals found to have a chronic and recurring addiction of cocaine are treated for a period of three weeks with a formulation comprising a protected complex of 4% procaine complexed with ascorbic acid, essentially the formulation disclosed above. The treatment comprises intramuscular injections of 200 to 300 mg of the formulation daily. After the three week treatment, nine of the eleven addicts avoid the use of cocaine or other narcotics for a period of from three to seven months. Additionally, attempts to use cocaine during the three week treatment period leads to aversion symptoms including vomiting, abdominal pain and muscle cramps.

It is apparent, therefore, that treatment with the composition of the present invention is effective in the treatment of individuals addicted to narcotics.

The above description is for the purpose of teaching the person of ordinary skill in the art how to practice the present invention, and it is not intended to detail all of those obvious modifications and variations of it which will become apparent to the skilled worker upon reading the description. It is intended, however, that all such obvious modifications and variations be included within the scope of the present invention which is defined by the following claims.

What is claimed is:

1. A composition for the treatment of age-related conditions which comprises procaine and a complexing agent capable of forming a protected complex with procaine, in an amount effective to reduce the symptoms of tinnitus and Alzheimer's disease.

2. The composition of claim 1 wherein said complexing agent comprises a composition selected from the group consisting of polysaccharides, glycols, ascorbic acid, pantothenic acid, amino acids and caffeine.

3. The composition of claim 2 wherein said complexing agent comprises ascorbic acid.

4. The composition of claim 1 wherein said age-related condition comprises Alzheimer's disease and said complexing agent comprises acetylsalicylic acid.

5. The composition of claim 1 which comprises about 1% to about 10% by weight of procaine.

6. The composition of claim 3 which comprises about 0.25% to about 10.0% by weight of ascorbic acid.

7. The composition of claim 1 which further comprises a compound selected from the group consisting of lidocaine, zinc citrate, anticholinesterases, anticortisol agents, and mixtures thereof.

8. The composition of claim 7 wherein said anticortisol agent is selected from the group consisting of dilantin and clonidine.

9. A method for treating age-related conditions in individuals comprising administering to the individual a tinnitus and Alzheimer's disease symptom reducing amount of procaine and a complexing agent capable of forming a protected complex with procaine.

10. The method of claim 9 wherein said complexing agent comprises a composition selected from the group consisting of polysaccharides, glycols, ascorbic acid, pantothenic acid, amino acids and caffeine.

11. The method of claim 10 wherein said complexing agent comprises ascorbic acid.

12. The method of claim 9 wherein said condition to be treated comprises Alzheimer's disease and said complexing agent comprises acetylsalicylic acid.

13. The method of claim 9 which comprises about 1% to about 10% by weight of procaine.

14. The method of claim 11 which comprises about 2.5% to about 25% by weight of ascorbic acid.

15. The method of claim 9 which further comprises a compound selected from the group consisting of lidocaine, zinc citrate, anticholinesterases, anticortisol agents, and mixtures thereof.

16. The method of claim 15 wherein said anticortisol agent is selected from the group consisting of dilantin and clonidine.

* * * * *